United States Patent
Gu et al.

(10) Patent No.: US 7,052,588 B2
(45) Date of Patent: May 30, 2006

(54) NANOTUBE CHEMICAL SENSOR BASED ON WORK FUNCTION OF ELECTRODES

(75) Inventors: Gang Gu, Palo Alto, CA (US); Lawrence S. Pan, Los Gatos, CA (US)

(73) Assignee: Molecular Nanosystems, Inc., Palo Alto, CA (US)

(*) Notice: Subject to any disclaimer, the term of this patent is extended or adjusted under 35 U.S.C. 154(b) by 0 days.

(21) Appl. No.: 10/723,117

(22) Filed: Nov. 26, 2003

(65) Prior Publication Data

US 2004/0104129 A1    Jun. 3, 2004

Related U.S. Application Data

(60) Provisional application No. 60/429,712, filed on Nov. 27, 2002.

(51) Int. Cl.
*G01N 27/327* (2006.01)
*G01N 27/414* (2006.01)

(52) U.S. Cl. .................. 204/403.01; 204/400; 257/253; 977/DIG. 1

(58) Field of Classification Search .............. 204/400, 204/403.01, 412, 431; 205/786.5, 792, 780, 205/775; 257/253; 977/DIG. 1
See application file for complete search history.

(56) References Cited

U.S. PATENT DOCUMENTS

| | | | | |
|---|---|---|---|---|
| 4,913,792 | A | * | 4/1990 | Nagata et al. ............... 204/412 |
| 5,156,972 | A | * | 10/1992 | Issachar ..................... 422/68.1 |
| 5,466,348 | A | * | 11/1995 | Holm-Kennedy ........... 205/775 |
| 6,528,020 | B1 | * | 3/2003 | Dai et al. ..................... 422/98 |

OTHER PUBLICATIONS

Cui et al, Science vol. 293, Aug. 2001, pp. 1289-1292.*
Kong et al, Science, vol. 287, Jan. 2000, pp. 622-625.*
Krstic et al, Electronic Properties of Novel Materials-Molecular Nanostructures, 2000, pp. 367-370.*
Dijksma et al, Anal. Chem., 73, pp. 901-907, Mar. 2001.*
Heo et al, App. Phys. Let., 81, pp. 3046-3048, Oct. 2002.*

* cited by examiner

*Primary Examiner*—Kaj K. Olsen
(74) *Attorney, Agent, or Firm*—Carr & Ferrell LLP (57) ABSTRACT

In one embodiment a method for sensing specific molecules is provided. The method comprises forming a nanoelement structure and forming two spaced apart electrodes in contact with the nanoelement structure, wherein at least one of the electrodes is capable of functioning as a sensing element to sense the specific molecules.

1 Claim, 10 Drawing Sheets

NANOTUBE CHEMICAL SENSOR BASED ON WORK FUNCTION OF ELECTRODES

CROSS-REFERENCE TO RELATED APPLICATIONS

The present patent application claims priority from provisional patent application No. 60/429,712, filed on Nov. 27, 2002, which is incorporated herein by reference.

FIELD OF THE INVENTION

This invention relates to nanotube devices that are sensors for specific molecules in gaseous and liquid analytes.

BACKGROUND

Nanotubes are a unique material with rich electrical and chemical properties and extreme mechanical strength, which makes them suitable for wide range of applications, including sensing molecules in gaseous and liquid analytes. Nanotube-based sensors hold great promise for such applications as environmental and industrial monitoring, transportation, medical devices, medical/clinical diagnostics, biotechnology for drug discovery, agricultural and consumer markets, national security, including both homeland defense and military operations. For general information regarding carbon nanotubes, their integration in sensing devices and their principles of work, reference may be made to the following U.S. Pat. Nos. 6,346,189; 6,232,706; 6,401,526; 6,528,020 and also Franklin, et al., *Appl. Phys. Lett.* 79, 4571 (2001) and Zhang et al., *Appl. Phys. Lett.* 79, 3155 (2001), all of which are incorporated herein for reference for all purposes.

Fluid sensors of which the inventors are aware, and which use carbon nanotubes and nanowires as sensing elements, take advantage of high surface-to-volume ratio of nanoelements (nanotubes and/or nanowires), which makes their electrical properties sensitive to surface-adsorbed molecules. The detection scheme in these sensors is based on chemical interactions between the surface atoms of the nanoelements, or materials attached to the surface atoms of the nanoelements, and the adsorbed molecules in gases and liquids. There are a number of drawbacks associated with the above-described sensors. One technique for making a hydrogen sensor includes coating a nanotube with individual nanoparticles of palladium (Pd). In this sensor, detection is based on charge transfer from a Pd nanoparticle, which adsorbs $H_2$ to the nanotube and results in lowering the nanotube conductance. The approach, however, has several shortcomings. For example, Pd nanoparticles have been found to be unstable due to their oxidation after exposure to $H_2$. This results in shorter life for the sensors.

Moreover, coating nanotubes or nanowires with a thin layer of Pd nanoparticles is inherently difficult to control and scale up, as it often leads to electrical short circuits in the device. This is particularly the case if the sensor design calls for an array of individual sensors for detection of different molecules placed in close proximity to each other.

Another disadvantage of existing nanotube/nanowire-based sensors relates to an inability to effectively, or at all, prevent non-specific interaction between the nanoelement and other molecules present in the surrounding environment. For example, a non-functionalized nanotube may be sensitive to $NO_2$. A device for detection of $H_2$ with nanotubes coated with particles of Pd reacts to both $H_2$ and $NO_2$ if molecules of both gases are simultaneously present, since parts of the nanotube are functionalized with Pd, and parts are not.

SUMMARY OF THE INVENTION

According to one aspect of the invention, there is provided a method for sensing specific molecules, the method comprising forming a nanoelement structure and forming two spaced apart electrodes in contact with the nanoelement structure, wherein at least one of the electrodes is capable of functioning as a sensing element to sense the specific molecules.

According to a second aspect of the invention, there is provided a method for sensing specific molecules, the method comprising forming a nanoelement structure, and forming two electrodes in contact with the nanoelement structure, wherein the Schottky barrier defined between at least one of the electrodes and the nanoelement structure enables the electrode to function as a sensor for the specific molecules According to a third aspect of the invention, there is provided a device for sensing specific molecules, the device comprising a nanostructure; and two electrodes connected by the nanostructure, wherein at least one electrode and a junction between the electrode and the nanostructure defines a sensing element for the specific molecules.

According to a fourth aspect of the invention, a device for sensing fluids, the device comprising at least one nanoelement; a first electrode and a second electrode connected by the at least one nanoelement; a third gate electrode disposed between the first and second electrode, wherein at least one of the first and second electrodes and a junction between the electrode and the at least one nanoelement defines a sensing element for the specific molecules; and wherein a gate voltage applied to the third gate electrode changes the Schottky barrier at the junction.

According to a fifth aspect of the invention, there is provided a field-effect transistor device, comprising at least one nanoelement; and a first and a second electrode connected by the or each nanoelement, wherein at least one of the first and second electrodes includes palladium.

BRIEF DESCRIPTION OF THE DRAWINGS

The invention is described by way of example with reference to the accompanying drawings, wherein.

DETAILED DESCRIPTION

In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Figure 1:
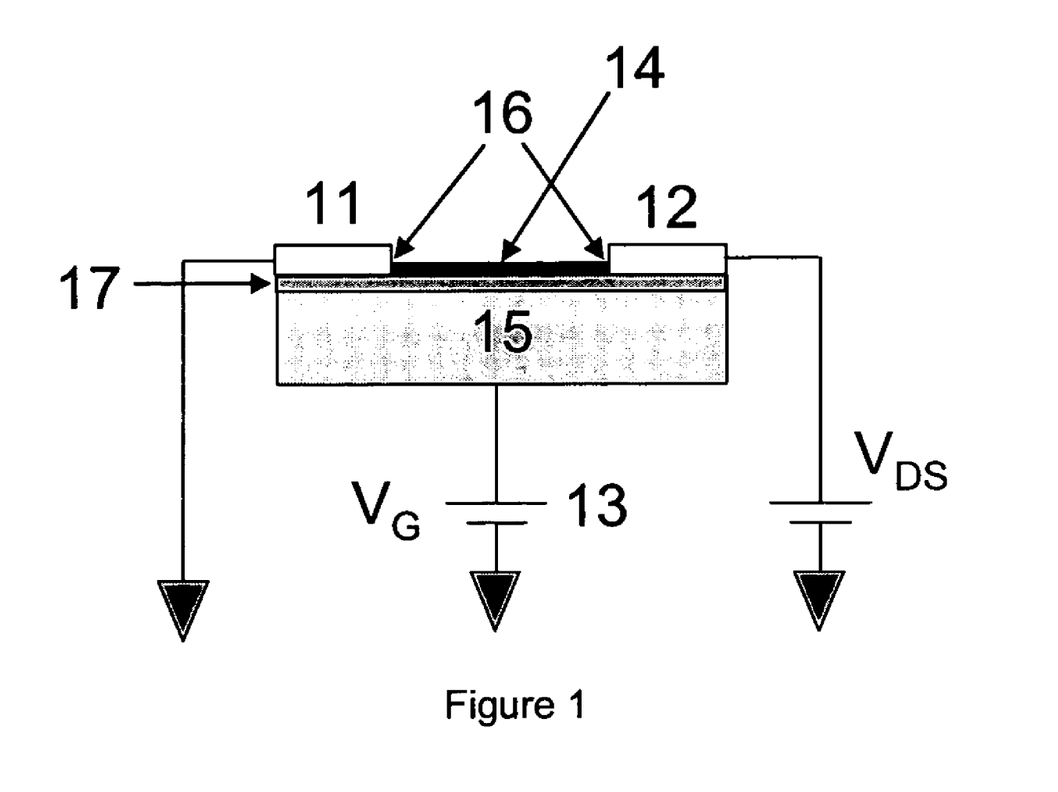
FIG. 1 is a schematic diagram of a nanotube electronic device in accordance with one embodiment of the invention.

The basic structure for a nanotube sensor is shown in FIG. 1. Each sensor includes a source electrode 11, a drain electrode 12, an optional gate electrode 13, and at least one nanotube or a network of nanotubes 14 connecting the source and the drain to form a field-effect transistor, if the gate electrode 13 is present. The device is fabricated on a substrate 15, which may be any insulating material, for example silica based, or any conducting material, for example silicon, provided that there is an insulating layer 17 between the said conducting substrate and the said electrodes 11 and 12 and nanotubes 14. A junction 16 between the nanotubes 14 and at least one of the electrodes 11, 12 acts as a sensing element. Specificity for particular molecules in a fluid analyte is controlled by the choice of material used for at least one of the electrodes 11, 12. The nanotubes 14 may be single-walled carbon nanotubes (SWNT), having a diameter of between 1 to 2 nm. Further, the nanotubes 14 may comprise a single tube, multiple tubes or a network of interconnected tubes. In some embodiments, the nanotubes 14 may be multi-walled nanotubes (MWNT). The nanotubes 14 may be semiconducting depending on the chirality of the nanotube. At least one of the electrodes 11 and 12 may be of metal or an alloy. For example, the electrodes 11, 12 may be of Ti, Pd, Au. It should be noted that while the present invention is described using carbon based nanotubes this is intended to be non-limiting. Thus, nanotubes made of materials other than carbon, e.g., silicon nanowires and inorganic nanorods, may also be used.

Figure 2A:
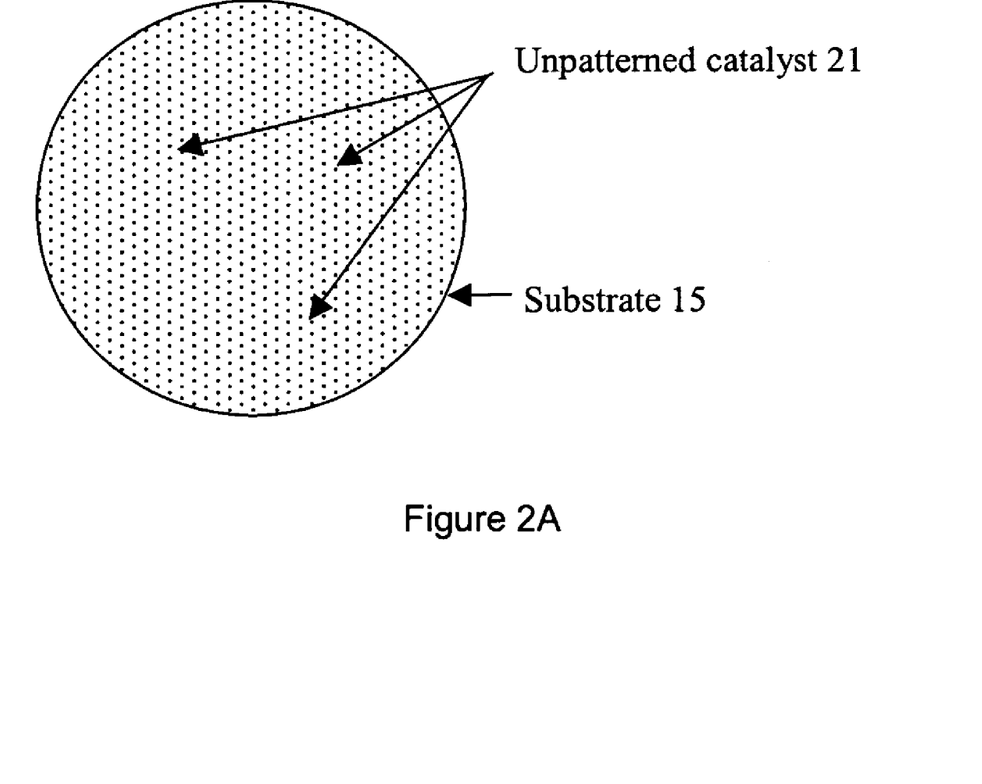
FIG. 2A is a schematic top view of a substrate with unpatterned catalyst.
Figure 2B:
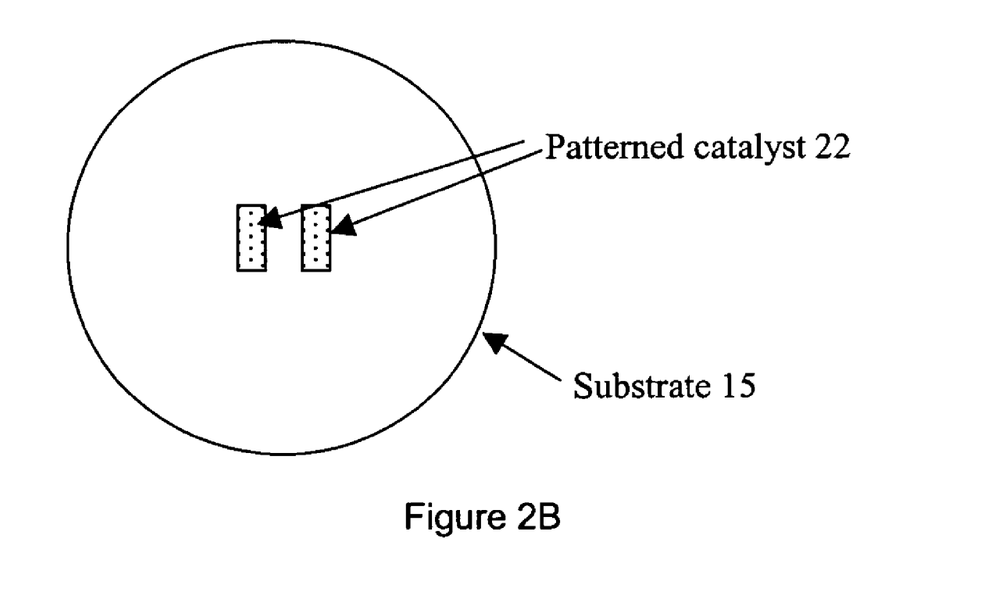
FIG. 2B is a schematic top view of a substrate with patterned catalyst.
Figure 3A:
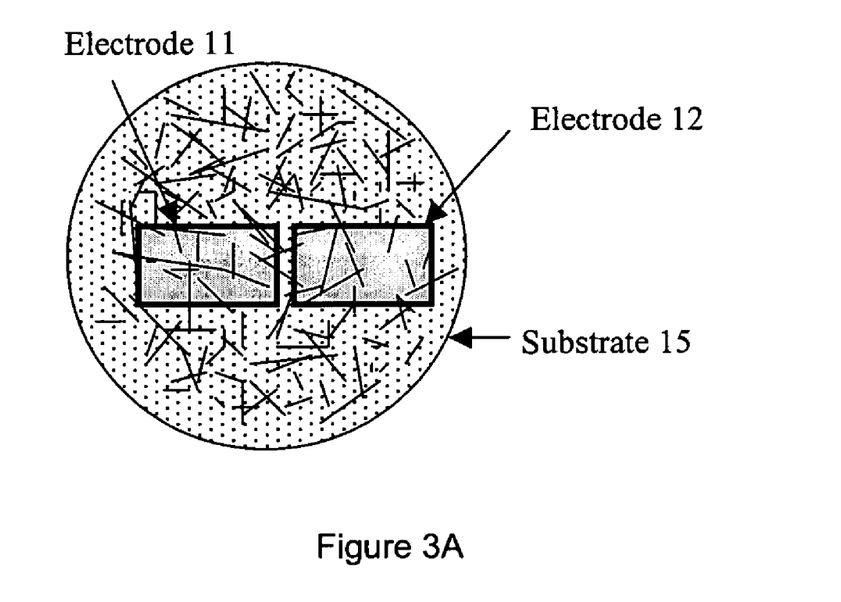
FIG. 3A is a schematic top view of a substrate with nanotubes and patterned metal contacts for the substrate with unpatterned catalyst.
Figure 3B:
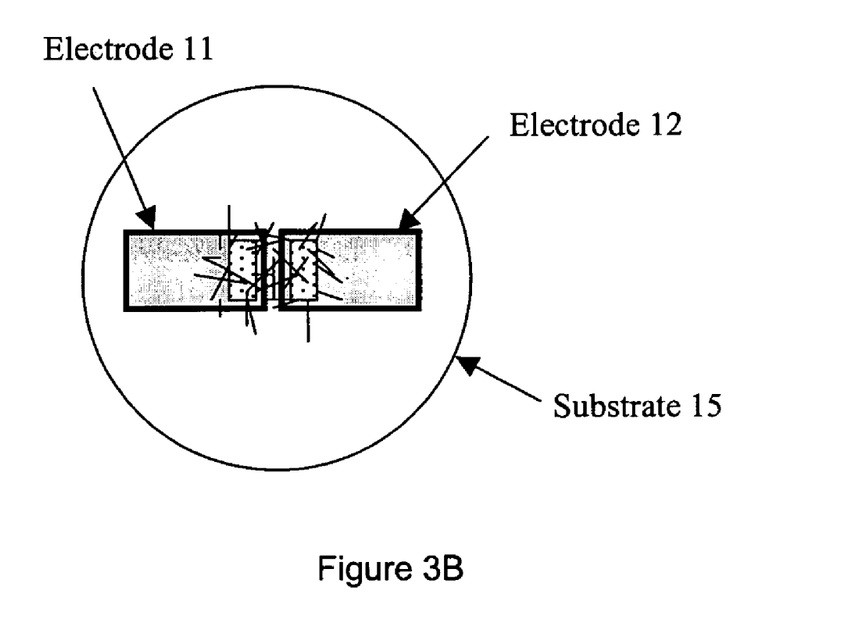
FIG. 3B is a schematic top view of a substrate with nanotubes and patterned metal contacts for the substrate with patterned catalyst.

The fabrication of carbon nanotube sensors may be based on nanotubes grown from an unpatterned catalyst 21 over a substrate 15, as illustrated in FIG. 2A. Alternatively the fabrication may be based on a patterned catalyst 22 over a substrate 15 as illustrated in FIG. 2B. Catalyst sites 21 or 22 on a substrate 15 lead to the growth of nanotubes from these sites. Following either unpatterned or patterned catalyst growth, optical lithography is then used for placing metal electrodes 11 and 12 to connect to the nanotubes in a controlled manner, as shown in FIG. 3A for the unpatterned catalyst and in FIG. 3B for the patterned catalyst. One procedure includes the following steps:

(1) catalytic particles are attached to the entire surface of the substrate 15 for unpatterned growth (FIG. 3A) or patterned on a substrate to form catalyst arrays for patterned growth (FIG. 3B). The patterning is done by a shadow mask or a photolithography technique.

(2) SWNTs are then grown by chemical vapor deposition from the catalyst sites.

(3) metal electrodes 11 and 12 are then placed onto SWNTs grown from the catalyst patterns by an optical lithography, metallization and liftoff procedure. In the case of patterned growth, this lithography step may involve optical alignment in registry with the catalyst patterns (See FIG. 3B). Growth by CVD combined with the microfabrication approach is a scalable approach to produce nanotube electronic devices including sensors.

The resistance of a nanotube device comprises channel resistance and contact resistance. Channel resistance is the resistance from one end of the nanotube 14 to the other, whereas contact resistance is the resistance between the metal contacts 11, 12, and the nanotube 14. Contact resistance is defined by the Schottky barrier (work function) that forms at the metal-nanotube junction 16. A change in the work function of the metal can change the contact resistance dramatically. The work function of a particular metal may be changed upon exposure to specific chemicals. By using this principle a nanotube-based sensor can be tailored to be selective to specific molecules in fluids. In one embodiment of the invention, the work function change of at least one of the electrodes 11 and 12 of a nanotube device is used for sensing molecules in fluids as can be seen from the following examples.

Working examples for the sensing of $H_2$ with Pd electrodes and sensing of $H_2S$ with Au electrodes are shown in Examples 1 and 2 below. It should be noted that while Pd and Au electrodes were used in the examples, Pd alloys such as PdNi and gold alloys such as AuPd may also be used.

In the Examples 1 and 2 that follow, a nanotube electronic sensor was fabricated by patterned growth of SWNTs on full 4-inch $SiO_2$/Si wafers. A $SiO_2$/Si wafer was first fabricated to get the alignment marks by standard photolithography with 1 μm Shipley 3612 as the photoresist. Then the patterned catalyst islands were fabricated with a quartz mask and dry etching on PMMA and Shipley 3612 coated silicon wafer. Afterwards a thin catalyst layer of suspension consisting of 15 ml methanol, 0.05 mmol $Fe(NO_3)_3 9H_2O$, 0.015 mmol $MoO_2(acac)_2$, and 15 mg Degussa alumina nanoparticles was coated on the patterned substrate. After lifting off with acetone, single-walled carbon nanotubes were grown at 900° C. for 7 min with 3.375 SLM $CH_4$ and 0.281 SLM $H_2$. After tube growth, standard photolithography was applied again for metal electrodes with alignment marks. Ti, Pd and Au have been used as the electrodes materials, with a highly doped Si wafer used as a backgate. The thickness of the thermal oxide layer of $SiO_2$ is about 100–1000 nm. Cleaning procedures were applied by heating the devices in acetone at 50° C. for 1 hour and then on a hot plate at 300° C. for 1 hour to provide a clean surface after lift-off.

EXAMPLE 1

Figure 4A:
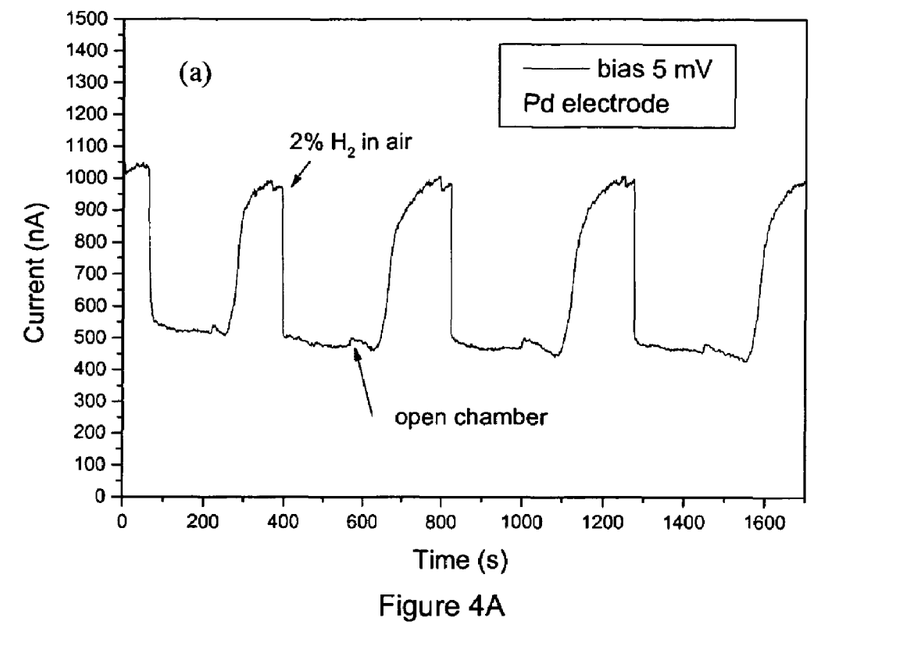
FIG. 4A is a graph illustrating the response of a nanotube device with Pd electrodes in accordance with one embodiment of the invention.
Figure 4B:
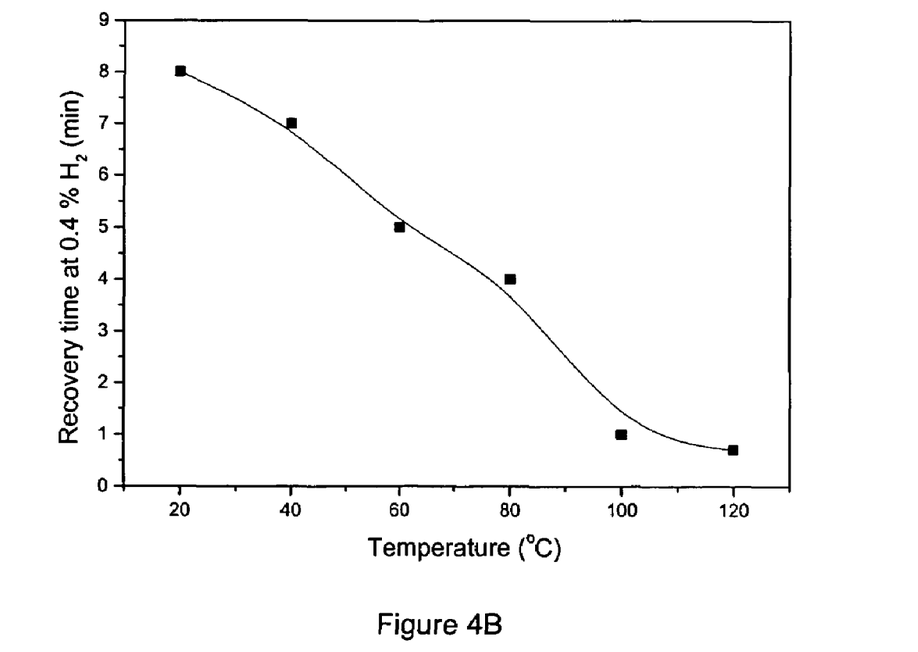
FIG. 4B is graph illustrating the recovery time for 0.4% $H_2$ at different operating temperatures.

For sensing $H_2$, devices were fabricated as described. However, the nanotubes were not coated with nanoparticles of Pd as in prior art nanotube and nanowire sensors, but instead the metal contacts 11 and 12 in this case were prepared by depositing 50 nm Pd using electron-beam evaporation. Devices were diced and then wire-bonded to chip-carriers for gas sensing experiments. When the device was exposed to 2% $H_2$ in air, a rapid current decrease was observed, as shown in FIG. 4A. The device quickly recovered to baseline current after purging of $H_2$ gas and exposing to air for about 5 min. FIG. 4A shows this procedure repeated 4 times. The adsorbed hydrogen gas changed the work function of the Pd electrode 11, 12, giving rise to the rapid current decrease. Upon exposure to air, the dissolved atomic hydrogen in Pd electrodes reacted with oxygen in air resulting in the recovery of $H_2$ sensor. Heating the sensor at a moderate temperature shortened the recovery time as shown in FIG. 4B. As a control, a device with Ti electrodes connected to nanotubes did not show a response upon exposure to 2% $H_2$.

EXAMPLE 2

Figure 5:
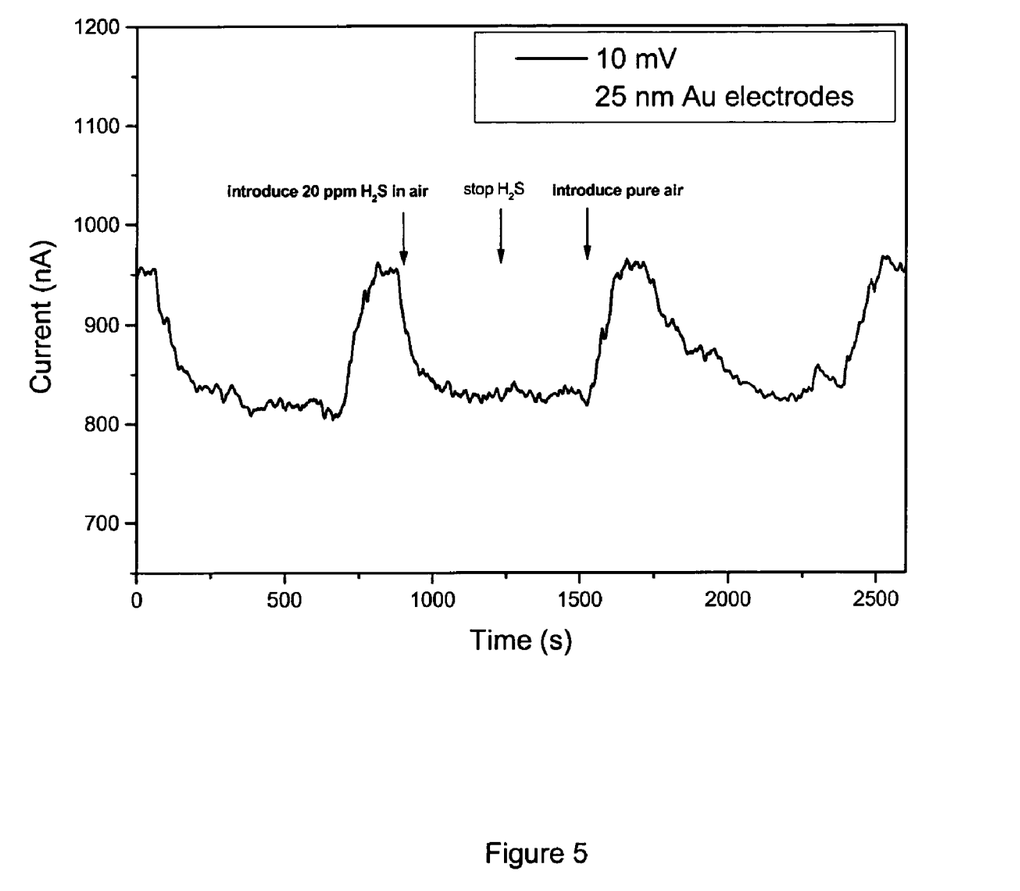
FIG. 5 is a graph illustrating the response of a nanotube device with Au electrodes in accordance with one embodiment of the invention.

For sensing of $H_2S$, devices were fabricated as described, and instead of depositing nanoparticles of gold on nanotubes 14 as would be done in prior art sensors, the metal contacts in this case were prepared by depositing 25 nm gold using electron-beam evaporation. FIG. 5 shows the response of the device to exposure of 20 ppm $H_2S$ in air, carried out twice. When the device was exposed to 20 ppm $H_2S$, a rapid current decrease was observed. The device quickly recovered to baseline after purging of $H_2S$ gas and exposing to air. To confirm that the gold electrodes had functioned as the $H_2S$ sensing element, a device with Ti electrodes connected to nanotubes did not show a response upon exposure to 20 ppm $H_2S$.

Figure 6A:
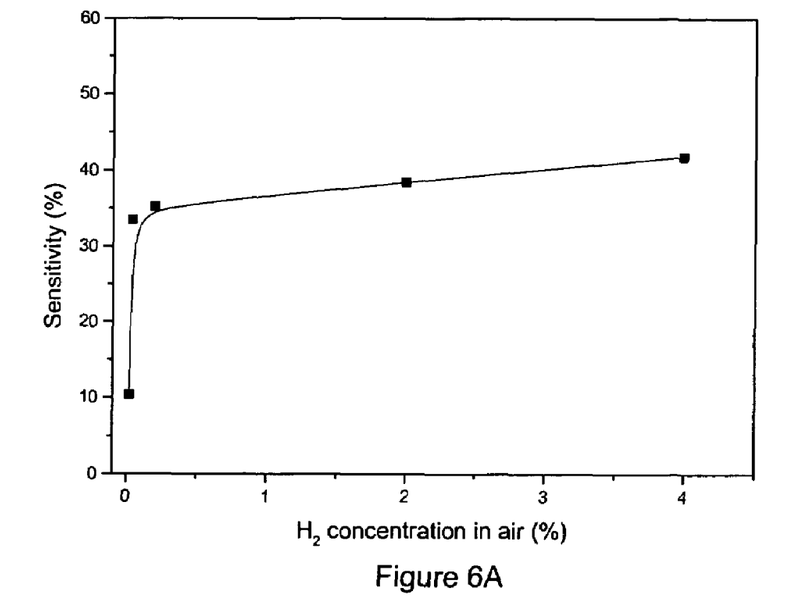
FIG. 6A is a graph illustrating sensitivity dependence on different $H_2$ concentrations without gate voltage.
Figure 6B:
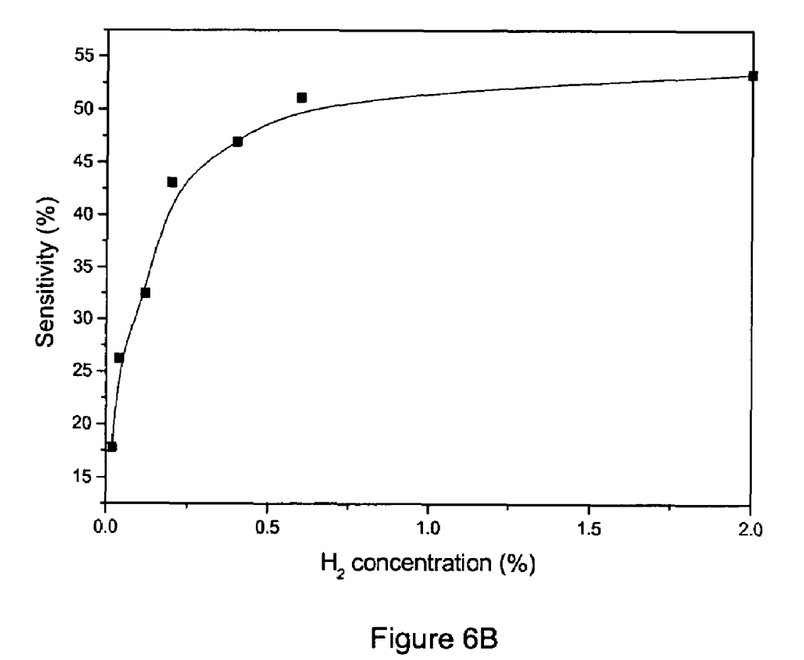
FIG. 6B is a graph illustrating sensitivity dependence on different $H_2$ concentrations with −5 V gate voltage, the sensitivity being defined as conductance difference before sensing and after sensing divided by base conductance.

FIGS. 6A and 6B show the sensitivity dependence of a nanotube device from Example 2 on different $H_2$ concentrations without application of a gate voltage (FIG. 6A) and with −5 V gate voltage on (FIG. 6B). The sensitivity is defined as the conductance difference before and after sensing divided by the base conductance. It was demonstrated that the linearity and sensitivity of a nanotube device can be improved by applying −5 V gate voltage during sensing. Negative gate can decrease the contact resistance and result in a wider linear region for sensing. With −5 V gating a linear response on $H_2$ concentration up to 300 ppm was obtained, as shown in FIG. 6B.

For the following examples 3 and 4, an iron-based catalyst was deposited on wafers homogenously. The Fe-containing nanoparticle formation was achieved by immersing the $SiO_2$/Si substrate into a scintillation vial containing 10 mL of water and 10 uL of 10 mM $FeCl_3 6H_2O$ (aq), followed by immediate addition of 100 uL of 40 mM $NH_2OH$ HCl-(aq) into the vial. After a few seconds stirring, the substrate was allowed to soak in the solution for a certain period of time (10 s to 5 min) before being taken out of the solution, rinsed consecutively with water, acetone, and isopropyl alcohol, and dried. After the liquid phase deposition process, the substrate was calcined in air at 800 C for 5 min. Nanotube growth was performed with chemical vapor deposition of $CH_4$ and $H_2$ in a 6 inch quartz tube at 900 C degree. Mechanical shadow masks were used for metal pad deposition. Metal deposition of Pd was performed by DC sputtering with a power of 50 W and a pressure of $5\times10^{-3}$ torr. The thickness of the metal was controlled to be 20 nm by sputtering time. Alternatively, instead of mechanical shadow masks, deep UV lithography was also used to fabricate devices, and polymethylmetharcylate (PMMA) was used as resist. After deep UV exposure and development, Au/Pd metals were used as electrodes. Firstly 20 nm Pd was sputtered with a power of 50 W and a pressure of $5\times10^{-3}$ torr, subsequently 20 nm Au was sputtered with the same power and pressure. Acetone was used for lift-off. The wafer was diced to get chips for testing. Afterwards chips were cleaned in Ar atmosphere at 200 C. degree for 30 min.

EXAMPLE 3

Figure 7:
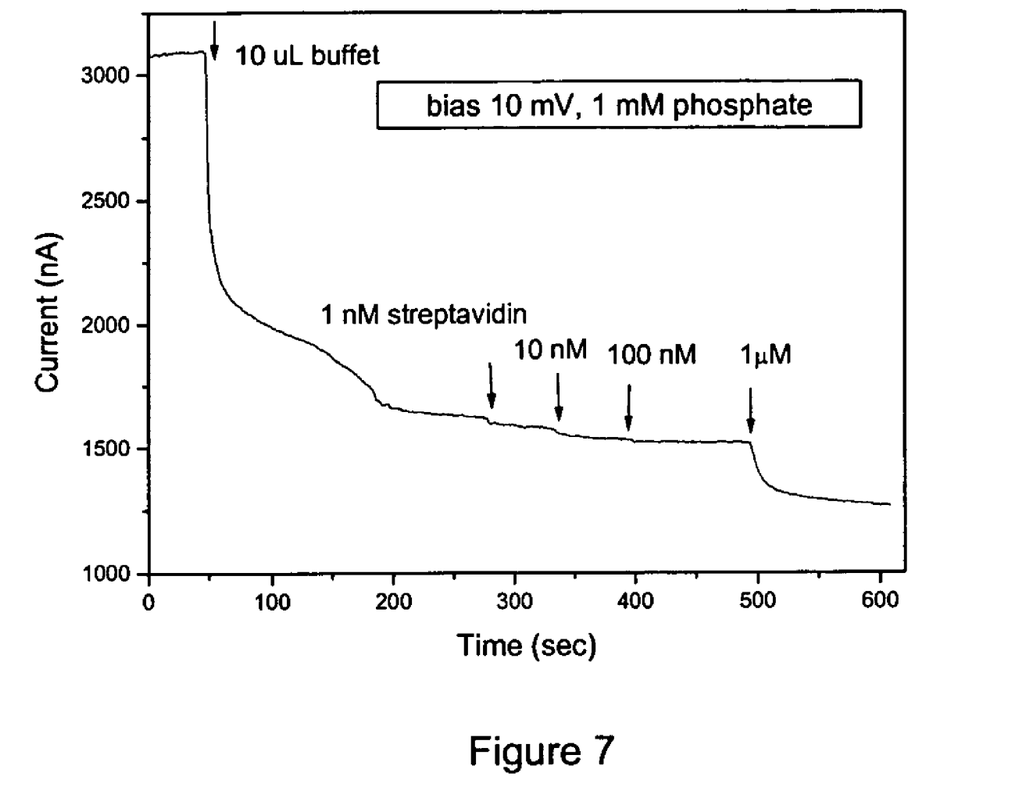
FIG. 7 shows the real time current measurement with different concentrations of strepavidin.
Figure 8A:
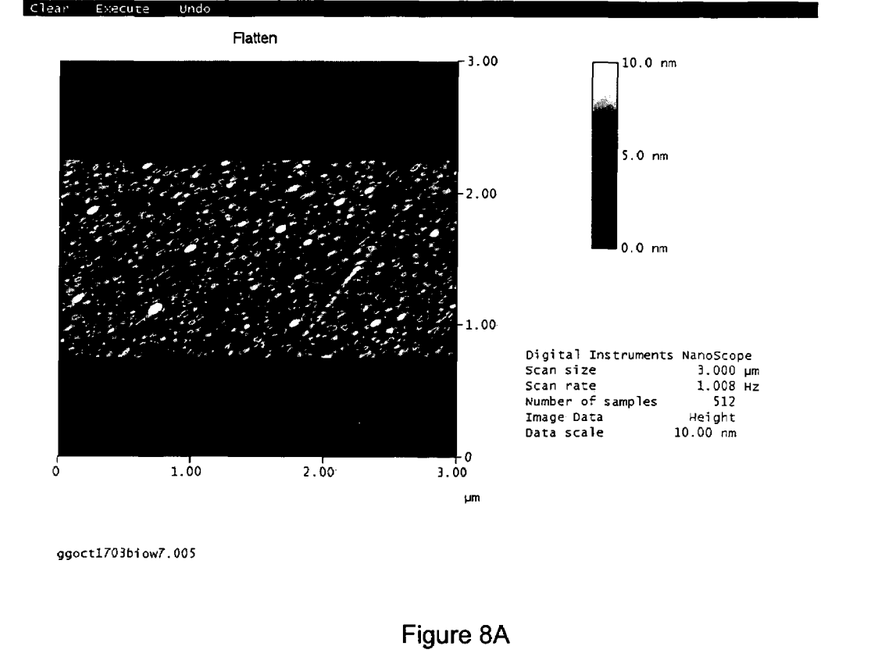
FIG. 8A is an AFM (atomic force microscope) image of an electrode before sensing.
Figure 8B:
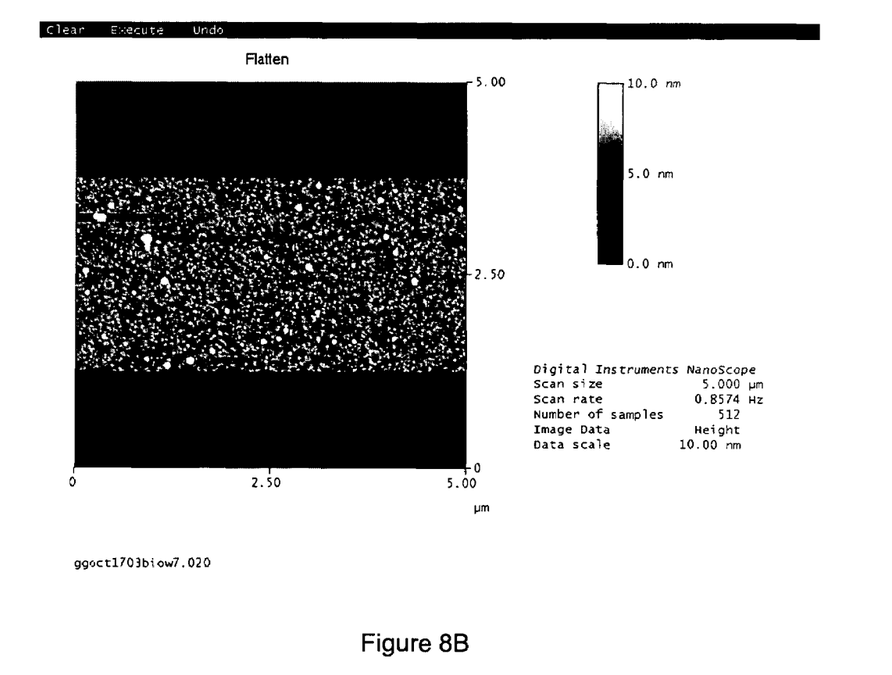
FIG. 8B is an AFM image of an electrode after sensing.

For sensing of streptavidin, devices were fabricated as described above. To test the device for streptavidin, 1 mM phosphate solution was used as buffer, and 1 nM to 1 µM streptavidin in 1 mM phosphate solvent was introduced sequentially, with a constant bias voltage of 10 mV being applied between the two electrodes. During this time, the current was monitored with Keithley 237. The result was shown in FIG. 7. A measurable resistance change was observed when 1 nM streptavidin was introduced. The resistance change increases with the streptavidin concentration. After sensing 1 µM streptavidin, the devices were imaged with an atomic force microscope. The substrate and Au/Pd electrodes were found to be coated with streptavidin. Control experiments found that nanotubes are not sensitive to streptavidin after passivation of Au/Pd electrodes with protein-resistant self-assembled monolayers of methoxy-(polyethylene glycol)-thiol. AFM images of a Au/Pd electrode before sensing and after sensing streptavidin are shown in FIG. 8A and FIG. 8B, respectively. After sensing, the electrode was coated with a sub-monolayer of streptavidin, which is consistent with the results of surface plasmon resonance (J.-J. Gau et al, Biosensors & Bioelectronics 16 (2001), 745) which indicate a sub-monolayer coverage of streptavidin. The absorbed streptavidin introduced dipoles which change the work function of the electrodes, therefore changing the contact resistance, and finally the conductance of the device.

EXAMPLE 4

Figure 9:
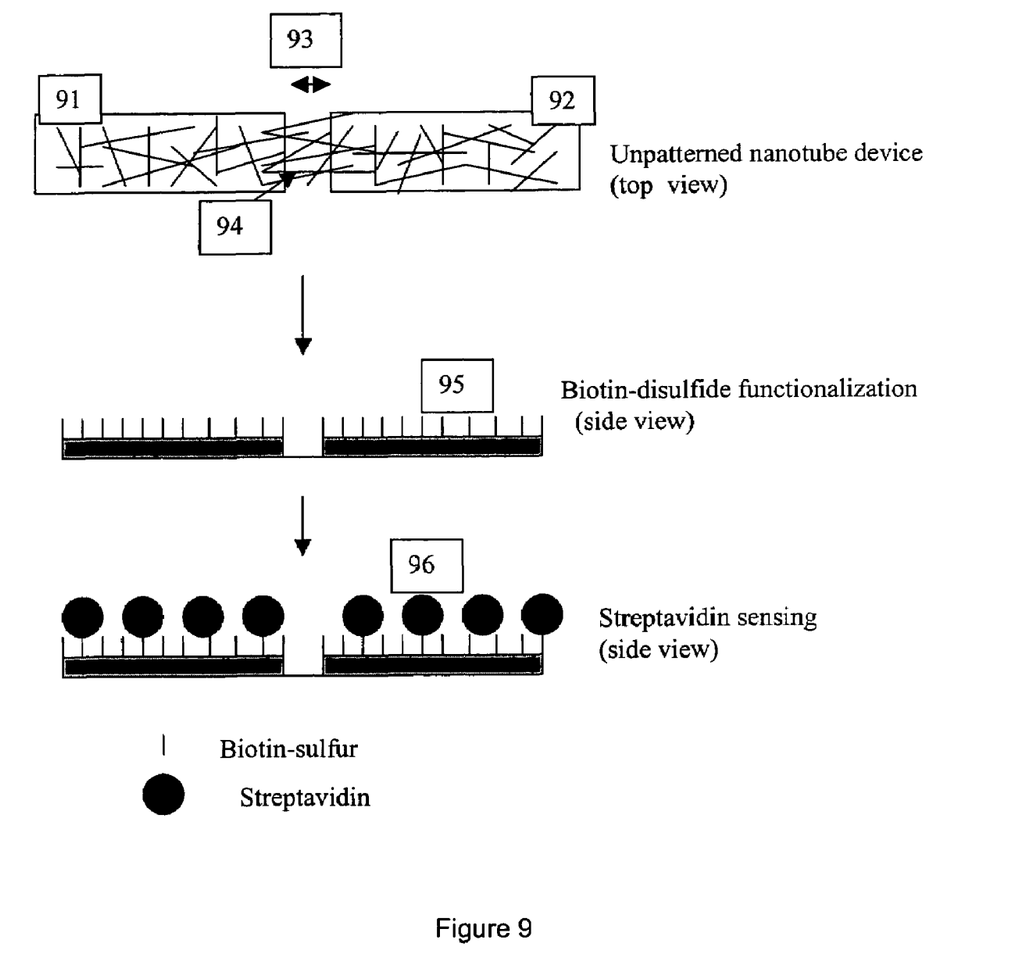
FIG. 9 are diagrams illustrating the sensing of streptavidin after biotin-immobilization.
Figure 10:
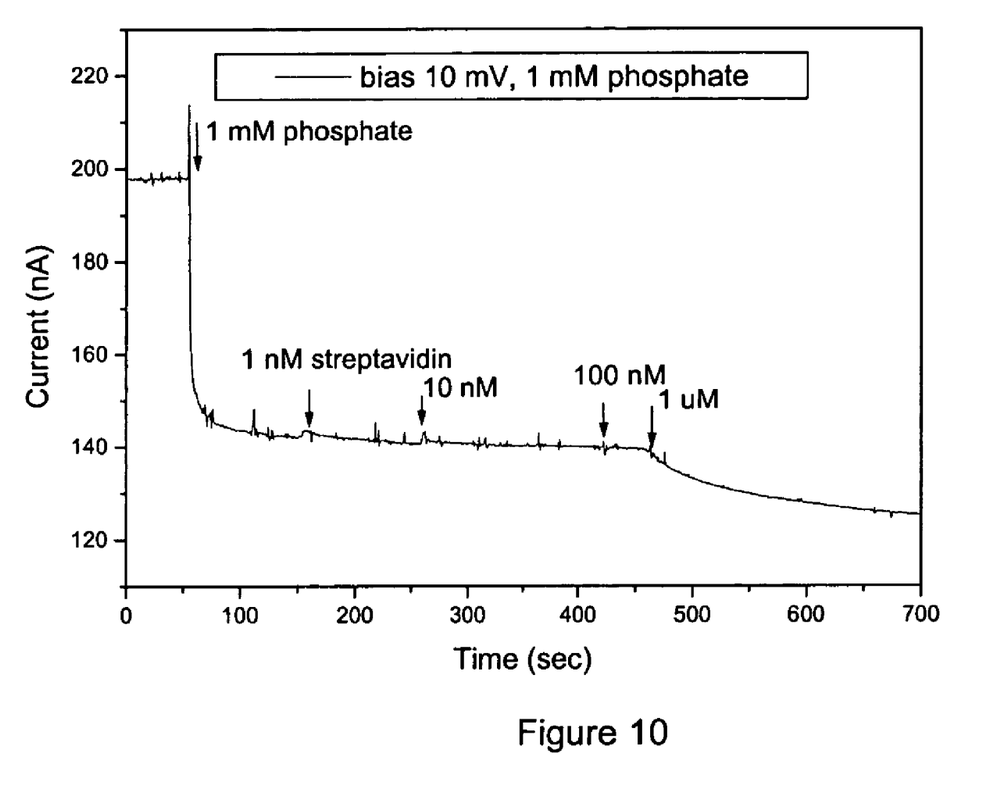
FIG. 10 shows a real-time current measurement when streptavidin with different concentration was added. 333 nM strepavidin induced an obvious current decrease.

For sensing of streptavidin in another way, devices were fabricated as described above. The metal contacts in this case were modified by adding biotin. The procedure is illustrated in FIG. 9. The source and drain electrodes 91 and 92 of an unpatterned device with gap 93 and nanotubes 94 were modified with a biotinylated self-assembled monolayer (SAM) 95 by incubating the device with a 1 mM ethanol solution of 2-(biotinamido-ethylamido)-3,3'-dithioldipropionic acid N-hydroxysuccinimide ester (biotin-disulfide) for 2 hours. The devices were rinsed with ethanol and dried with argon. Poly-dimethylsiloxane (PDMS) stamps were used to confine the liquid for sensing. 1 mM phosphate with a pH value of 7.2 was used as the buffer and solvent for streptavidin 96 of different concentrations. A constant bias voltage of 10 mV was applied between the two electrodes for real time sensing measurements. 10 µL 1 mM sodium phosphate was added as a buffer before introducing streptavidin, and then 5 µL streptavidin with different concentrations was introduced. FIG. 10 shows a real-time current measurement as streptavidin with different concentrations was added. 333 nM strepavidin induced an obvious current decrease, labeled as 1 micro molar, before dilution. Immobilization of biotin-sulfide on the surface introduced surface dipoles, and after binding with streptavidin these dipoles vary, and hence induce a work function change of the Au/Pd electrodes. Charge transfer between the carbon nanotube and the electrode occurred because of the work function change. The charge transfer results in a contact resistance change. Experimentally it has been found that nanotubes are ballistic in electrical transport, indicating that the channel resistance is negligible. However for silicon nanowires, previous studies indicate that diffusive (channel) conduction dominates. Therefore more sensitive sensors can be fabricated with carbon nanotubes based on the work function change of electrodes.

The selectivity of the sensors may be improved by having nanotubes or nanowires 14 uniformly coated with protective layers, such as polymers, that will block other molecules from contact with nanotubes or nanowires. The device will still function because the electrodes and the junction between electrodes 11, 12 and nanotubes or nanowires 14 will remain uncoated. In one embodiment, a gate voltage may be applied to the gate electrode 13 to alter the Schottky barrier at the junction thereby to change the sensitivity of the sensor. The gate voltage may also be applied to change the recovery time of the sensor. Another advantage of this approach is better ability to produce sensing devices with wider dynamic sensing range, because the effective work function of alloy in the electrode 11, 12 can be continuously adjusted by different compositions of alloys.

By using Pd alloy-based thin film electrodes 11, 12, the Pd becomes a stable material, thereby resulting in a higher longevity for the sensors of the present invention. The sensors of the present invention also exhibit higher sensitivity, because instead of using a charge transfer as a mechanism of molecule detection, the sensors of the present invention employ a contact barrier between the electrodes of the sensor and the nanotube(s) in which case electrical current is exponentially dependent on the barrier. Another advantage of the sensors of the present invention is that they can be fabricated by a simplified process, because production of thin-film Pd alloys is a well understood and widely established industrial process. This will result in a lower manufacturing cost and better reproducibility for the servicing devices of the present invention.

What is claimed is:

1. A bio-molecule sensor comprising:
a substrate;
a nanotube having first and second ends disposed on the substrate; and
a pair of electrodes disposed on the substrate, each electrode contacting an end of the nanotube, one electrode comprising a surface layer including a molecule with an affinity for the bio-molecule, wherein the surface layer includes biotin.

* * * * *